United States Patent [19]

Korosec et al.

[11] 4,376,055

[45] Mar. 8, 1983

[54] PROCESS FOR MAKING HIGHLY SULFURIZED OXYMOLYBDENUM ORGANO COMPOUNDS

[75] Inventors: Philip S. Korosec, Ballwin, Mo.; Litt Fredric A., University Heights, Ohio

[73] Assignee: Elco Corporation, Cleveland, Ohio

[21] Appl. No.: 74,901

[22] Filed: Sep. 12, 1979

[51] Int. Cl.³ .............................................. C10M 1/48
[52] U.S. Cl. .............................................. 252/32.7 E
[58] Field of Search ................. 260/429 K, 429 R; 252/32.7 E

[56] References Cited

U.S. PATENT DOCUMENTS

| | | | |
|---|---|---|---|
| 3,400,140 | 9/1968 | Rowan et al. | 252/32.7 E |
| 3,402,188 | 9/1968 | Wiese | 252/32.7 E |
| 3,733,345 | 5/1973 | Chiola et al. | 260/429 K |
| 4,202,781 | 5/1980 | Sabol et al. | 252/32.7 HC |

*Primary Examiner*—Charles F. Warren
*Assistant Examiner*—Y. Harris-Smith

[57] ABSTRACT

A process for preparing sulfurized oxymolybdenum organophosphorodithio compounds is described which includes the steps of (A) reacting at reflux in an inert solvent for at least one hour (1) an oxide of molybdenum, (2) a sulfurizing compound selected from the group consisting of sodium hydrosulfide and sodium monosulfide, and (3) a dialkylphosphorodithioic acid, and then (B) recovering the reaction product. Certain of these compounds have fuel efficient characteristics, as well as extreme pressure (E.P.) performance when blended into mineral oils, greases or synthetic lubricating fluids.

4 Claims, No Drawings

PROCESS FOR MAKING HIGHLY SULFURIZED OXYMOLYBDENUM ORGANO COMPOUNDS

BRIEF SUMMARY OF THE INVENTION

It has long been recognized that molybdenum compounds, particularly molybdenum disulfide ($MoS_2$), can help reduce wear and friction and act as extreme pressure (E.P.) agents. The reduction of friction in the moving parts of a passenger car has become of extreme importance in recent years since this improves the efficiency of the engine by requiring less relative power. Independent studies by several companies have shown that a 2 to 2.5% improvement in gasoline mileage can be expected if $MoS_2$ is added to crankcase oil.

Unfortunately the $MoS_2$ is insoluble in mineral oil and must be introduced as a dispersion. This could ultimately cause filter plugging if the dispersion falls apart. Also less friction modification would occur if the additive cannot reach the moving parts in the upper parts of engine due to drop out in the oil pan area.

Oil soluble sulfurized oxymolybdenum organo compounds can solve the additive drop out problems. These were prepared in the prior art from molybdic oxide ($MoO_3$) by first dissolving the $MoO_3$ in a base such as sodium hydroxide, acidifying the solution to obtain an aqueous solution of a complex molybdenum-covalent oxygen ion such as $[O_3Mo-O-MoO_3]^{--}$ for example and then adding an organophosphorodithioic acid reactant to form a sulfurized oxymolybdenum organophosphorodithioate. In methods of this type the sulfurization sulfur is evidently supplied solely by the dithioic acid reactant and the degree of sulfurization of the final product is quite limited as is the yield. This may be due to the fact that part of the reactant is used only for its sulfur content. Products prepared by this method also are corrosive towards copper and copper containing alloys probably due also to the use of excess dithioic acid. This limits the use of such product in certain engine, transmission and gear oil applications.

This invention relates to a method for preparing sulfurized oxymolybdenum organo compounds having superior lubricant additive characteristics.

In accordance with the present invention, molybdic oxide is first reacted with a sulfhydrate, a sulfide or an equivalent sulfur containing compound. While the acidified solution resulting from this reaction would be expected to yield $[O_3Mo-S-MoO_3]^{--}$ plus $H_2S$, such is not the case as is evidenced by the fact that only a trace of $H_2S$ is formed. Apparently the initial sulfomolybdenum intermediate of the present process is significantly more complex than would be expected and this departure from the expected chemical structure is reflected in the structure and characteristics of the ultimate sulfurized molybdenum organo compounds obtained in the practice of the method of the present invention. These compounds are produced by reacting the initial unknown sulfo-molybdenum intermediate of the present process with a suitable ligand reactant of the types hereinafter described. Since the sulfurization is accomplished at the intermediate stage, it is not required that the ligand reactant be sulfur-containing as is required in the practice of the prior art. However, organic thio ligand reactants may be reacted with the unknown intermediate in the practice of the present invention.

When dithioic acid reactants are used higher yields of the metallic organo molybdenum compound occurs, less by-product formation is noted and the finished reaction mixture is less corrosive towards copper and copper containing alloys.

The following examples are set forth as representing preferred embodiments of the present invention, but these examples are merely intended to illustrate the invention by the way of preferred examples without limiting the scope thereof.

DETAILED DESCRIPTION

Example I

Into a 5-liter 3-necked flask equipped with a stirrer, condenser, thermometer and addition funnel was placed 72 grams (0.5 mole) of molybdic oxide ($MoO_3$), 300 ml. of water and 300 ml. of methanol. To this mixture was added 93 grams (0.5 mole) of 30% sodium sulfhydrate (NaSH) with stirring. The temperature rose to 30° C. and the molybdic oxide dissolved. Next, 22.5 grams (0.23 mole) of 96% sulfuric acid was added drop-wise while keeping the temperature of the mixture below 50° C. The mixture was stirred for one (1) hour. Only a trace of $H_2S$ was evolved. Next, 327 grams of di(4-methyl-2-pentyl) phosphorodithioic acid in 300 grams of oil was added while heating the mixture to 80° C. After this addition was completed, the mixture was refluxed at 80° C. for two (2) hours, cooled and 500 ml. of hexane was added. The organic layer was separated and stripped of solvent under vacuum. The yield was 81% consisting of 565 grams of brownish liquid having the following analysis: Mo, 5.1%, S, 15.9%; P, 2.8%.

Example II

Into a 2-liter 3-necked flask equipped with stirrer, condenser, thermometer and addition funnel was placed 72 grams (0.5 mole) of molybdic oxide ($MoO_3$) and 300 ml. of water. To this mixture there was added 93 grams (0.5 mole) of a 30% solution of sodium sulfhydrate (NaSH) with stirring. The temperature rose to 30° C. and the molybdic oxide dissolved. Next, 23.5 grams (0.24 mole) of $H_2SO_4$ was added drop-wise keeping the temperature below 50° C. The mixture was stirred for one (1) hour. Only a trace of $H_2S$ was evolved. Next 464 grams (1.0 mole) of diisodecylphosphorodithioic acid in 200 grams of oil was added slowly and the mixture heated to 85° C. for six (6) hours. The mixture was then cooled, the organic layer was separated and then stripped of solvent. The yield was 88.8% consisting of 654 grams of brownish liquid having the following analysis: Mo, 6.2%; sulfur 7.8%; P, 3.22%.

Example III

Into a 3-necked flask equipped as in the preceding examples was placed 36 grams (0.25 mole) of molybdic oxide and 300 ml. of water. To this mixture was added with stirring 14 grams (0.11 mole) of 60% $Na_2S$ flakes. The temperature rose to 40° C. and the molybdic oxide dissolved.

Next, 10.3 grams (0.1 mole) of $H_2SO_4$ was added while holding the temperature at 55° C. Only a trace of $H_2S$ was evolved. On completion of the $H_2SO_4$ addition, 236 grams (0.5 mole) diisodecylphosphorodithioic acid was added drop-wise while heating to 110° C. for six hours, and was then cooled and 400 cc of hexane were added. The organic layer was then separated and stripped of solvent under vacuum to 130° C. The product analyzed as follows: Mo, 9.9%; S, 17.9%; P, 4.4%.

Example IV

Into a 3-necked flask equipped as in the preceding examples was placed 144 grams (1.0 mole) of molybdic oxide and 900 ml. of water. To this mixture was added 65 grams (0.5 mole) of 60% $Na_2S$ flakes. Solution was effected immediately. Next, 45.6 grams (0.45 mole) of $H_2SO_4$ were added while maintaining the temperature at 70° C. over the period of one-half hour. The mixture was then cooled to 60° C. 462 grams of dipropylphosphorodithioic acid was then added in one-half hour, after which the mixture was heated at 96° C. for four hours. The product was separated from the aqueous layer and stripped to remove solvents. Elemental analysis was as follows: Mo, 12.0%; S, 27.5%; P, 6.0%.

Example V

Into a 3-necked flask equipped as in the preceding examples was placed 144 grams (1.0 mole) of molybdic oxide and 900 ml of water. To this mixture was added 130 grams (1.0 mole) of 60% $Na_2S$ flakes, and the mixture stirred. 91.2 grams (0.9 mole) of $H_2SO_4$ was then added allowing the temperature to rise to 80° C. After this addition was completed, the mixture was cooled to 52° C. and 462 grams of dipropylphosphorodithioic acid was added over a two (2) hour period. To this solution a 125 cc of isopropanol was added. The mixture was then refluxed for seven (7) hours, cooled, separated and stripped of solvent. The product had an elemental analysis as follows: Mo, 7.2%; S, 23.6%; P, 6.4%.

Example VI

In a 3-necked flask equipped as in the preceding examples was placed 144 grams (1.0 mole) of molybdic oxide, 250 mo of isopropyl alcohol and 250 ml of water, and the resultant mixture heated to dissolve the molybdic oxide. With continued heating, 160 grams (1 mole) of NaSH was added slowly, after which was added 702 grams (2.0 mole) of di(4-methyl-2-pentyl)phosphorodithioic acid and 500 grams of 100 S.U.S. mineral oil. The temperature of this mixture was maintained within the range of 85°–90° C. for five hours while refluxing. After cooling overnight the aqueous and organic layers were separated in a separatory funnel, the organic layer stripped to 110° C. and filtered. The elemental analysis was as follows: Mo, 7.0%; S, 16.4%; P, 4.0%. The yield was 83.6% of theory.

Example VII

Into a twelve liter 3-necked flask equipped as in the preceding examples was placed 576 grams (4.0 moles) of molybdic oxide, 1,000 ml of isopropyl alcohol and 1,000 ml of water, and the resultant mixture heated to dissolve the molybdic oxide. With continued heating, 640 grams (4.0 moles) of NaSH was added slowly, after which was added 2,808 grams (8.0 moles) of di(4-methyl-2-pentyl)-phosphorodithioic acid and 2,000 grams of 100 S.U.S. mineral oil. The temperature of this mixture was maintained within the range of 85°–90° C. for five hours while refluxing. After cooling overnight the aqueous and organic layers were separated in a separatory funnel, the organic layer stripped to 110° C. and filtered. The elemental analysis was as follows: Mo, 11.0%; S, 16.0%; P, 2.9%.

Example VIII

Into a two liter 3-necked flask equipped as in the preceding examples was placed 72 grams (0.5 moles) of molybdic oxide, 100 ml of isobutyl alcohol and 100 ml of water and the resultant mixture heated to dissolve the molybdic oxide. The resultant mixture was cooled to below 50° C. and 6.5 grams of a 60% solution of $Na_2S$ was added with stirring over a period of 15 minutes. To this mixture was added 354 grams (1.0 mole) of di(2-ethyl hexyl)phosphorodithioic acid and the mixture heated to 95° C. to reflux for four hours. After cooling hexane was added and the mixture allowed to stand overnight. The organic layer was separated and stripped to 119° C. and then filtered. The yield of product was 98.2%, having an elemental analysis as follows: Mo, 8.9%; S, 14.5%; P, 6.8%.

Example IX

Into a two liter, 3-necked flask equipped as in the preceding examples was placed 36 grams (0.25 mole) of molybdic oxide, 60 ml of isopropyl alcohol and 60 ml water, which was heated and stirred until the molybdic oxide dissolved. 40 grams (0.25 moles) of NaSH was added to this mixture and while continuing the heating and stirring 125 grams of 100 S.U.S. mineral oil and 244 grams of dialkyl phosphorodithioic acid prepared from a $C_{12}$-$C_{18}$ alcohol was added. This mixture was heated to within the temperature range of 85°–90° C. and refluxed for 4½ hours. After cooling the organics were stripped to 110° C. and filtered. The elemental analysis was as follows: Mo, 4.0%; S, 8.2%; P, 2.3%.

Example X (Comparative)

Into a 3-necked flask equipped as in the preceding examples was placed 17.5 grams (0.44 moles) of sodium hydroxide pellets and 317.5 ml of water. After the sodium hydroxide dissolved, 72.0 grams (0.5 moles) of molybdic oxide was added and the mixture heated to 50° C. to effect solution. 25.7 grams (0.42 moles) of acetic acid was then added and the mixture cooled to 45° C. Next, 400 grams (1.0 moles) of diisodecylphosphorodithioic acid was added and the mixture heated to 90° C. for five hours. 250 ml of toluene was added during this heating step. The resultant mixture was poured into a separatory funnel and the aqueous layer separated. The organic layer was washed with 300 ml of water and stripped to 125° C./18 mm Hg. The yield was 359 grams. The product showed the following elemental analysis: Mo, 10.05%; S, 17.3%; P, 4.20%.

Example XI

Into a 50 liter, 3-necked flask equipped as in the preceding examples was placed 3,960 grams of iospropyl alcohol and 3,240 grams (22.5 moles) of molybdic oxide and the mixture stirred for ten minutes. Then 3600 grams (22.5 moles) of 35% NaSH solution was added and the resulting mixture stirred for ten minutes. Then 2,250 grams of oil was added together with 15,525 grams (45 moles) of di-(4-methyl-2-pentyl)phosphorodithioic acid. The whole mixture was heated to reflux and held at about 95° C. for 5 hours, after which it was stripped and filtered. The product had the following elemental analysis: Mo, 9.6%; S, 12.4%; P, 2.8%.

Example XII (Comparative)

Into a 5 liter 3-neck round bottom flask equipped with condenser, thermometer and stirrer was added 100 grams of $MoO_3$ (0.70 moles) and 600 ml of IN NaOH solution. (0.60). This mixture was heated-stirred to dissolve the $MoO_3$. 29.2 grams of $H_2SO_4$ (0.28 moles) was added slowly and temperature then brought to 49° C. at which time 490 grams of di(2-ethyl hexyl)phosphorodithioic acid (1.38 moles) was added. The mixture was then brought to reflux and held at approximately 95° C. for five hours. The reaction product was then cooled and poured into a separatory funnel. The product layer was separated and then washed with water then hexane was added. The hexane solution was then stripped of solvent yielding 513.3 grams of product which had the following analysis: Mo, 7.75%; S, 12.14%; P, 7.4%.

Example XIII

Into a 1 liter 3-necked round bottom flask equipped with thermometer, condenser and stirrer was placed 72 grams of $MoO_3$ (0.5 moles) and 300 ml of water. 35 grams of NaOH (50% solution) (0.44 moles) was mixed in and heated to effect solution of the $MoO_3$. 21.7 grams of $H_2SO_4$ (0.21 moles) was added drop-wise over 7' with a resulting exotherm of 3° C. to 69° C. The mixture was then cooled to 43° C. Next, 268 grams of an 80% diisopropyl phosphorodithioic acid 20% toluene mixture (1 mole) was added with stirring. The exotherm was to 48° C. The entire mixture was then heated to approximately 90° C. for 2 hours after which it was cooled in an ice bath. The mixture was first filtered and the filter cake then washed successively with water, methanol and hexane. The crude product was a yellow green solid which was then stirred into hexane for four (4) hours and filtered yielding a bright lemon solid melting at 130°–134° C.

Example XIV

In a 1 liter 3-necked round bottom flask equipped with thermometer, condenser and stirrer was placed 72 grams of $MoO_3$ (0.5 moles) and 300 ml of water. 82 grams of a 30% NaSH solution (0.44 moles) was mixed in and heated to effect solution of $MoO_3$. 21.7 grams of $H_2SO_4$ (0.21 moles) was added drop-wise over 7' with a resulting exotherm of 5° C. to 80° C. The mixture was then cooled to 43° C. Next 268 grams of an 80% diisopropylphosphorodithioic acid 20% toluene mixture (1 mole) was added with stirring. The exotherm was to 50° C. The mixture was then heated to 84° C. and held 2 hours after which it was cooled in an ice bath. The thick viscous material was washed successively with water, methanol and hexane through a Büchner funnel. The crude product was a light brown solid which was then stirred in hexane for 2 hours and filtered yielding a dull orange solid melting at 150°–153° C.

The preferred embodiment of this invention is that exemplified by Examples VI to IX wherein the molybdate solution is not neutralized prior to its reaction with any sulfur containing compound. It may be noted that on the average the analyses (by $P^{31}$ N.M.R. techniques) of the products of these examples show a proportionately higher percentage of metallic component. By-product formation therefore is less. In addition, the by-product mix is different. Example VIII was contrasted against Example XII by $P^{31}$ N.M.R. techniques. The data gathered showed that the metallic component (sulfomolybdenum compound) in Example VIII represented 54% of the mixture while in Example XII it was less than 40%. This represents a molybdenum incorporation or yield improvement of 35%.

Example VIII's by-product mix exhibited two new components representing 9% of the total but only 1.5% of the corrosive dithioic acid. Example XII's by-products contained 43% of the dithioic acid.

The effect of this by-product mix on copper corrosion can be shown by the following test where 30 grams of oil containing 1.5 wt. % of the additive is held for 48 hours at 150° C. in the presence of of pre-weighed and cleaned metal chips of copper, steel, aluminum and lead. In the case of 1.5 wt. % of Example VIII in oil the copper weight loss was 0.0022 mg/cm$^2$ while Example XII's was approximately twice as high with 0.0037 mg/cm$^2$ copper weight loss being noted.

The improved corrosion inhibition towards copper and copper alloys was further reflected when 1.1 wt. % of Example 1 was tested in a typical multi-graded (10W40) motor oil in the CRC L-38 bearing corrosion test. In this 40 hour single cylinder engine test a bearing made of a copper alloy is weighed before and after to determine its weight loss. A weight loss of only 21.8 mg was recorded and is well below the desired 40 mg maximum weight loss considered acceptable in this test.

The friction modification ability of these sulfomolybdenum products of the process of this invention have been demonstrated in the press fit test apparatus. The data shown in Table I indicates that these products have the same friction modifying ability as $MoS_2$ but at a concentration of elemental molybdenum in oil which is one-sixth (1/6) to one-tenth (1/10) lower. All the additives were run at 1 wt. % in oil. The friction coefficient (u) was determined initially, after 10 insertions of the pin into the bushing and after it stabilized (normally after 20 insertions of the pin into the bushing).

TABLE I

| Additive (1% in oil) | Mo, wt. % | Initial | 10× | Stabilized |
|---|---|---|---|---|
| Blank | — | 0.129 | 0.13 | — |
| MoS$_2$ | 60 | 0.074 | 0.058 | 0.047 |
| Example VI | 7.0 | 0.095 | 0.050 | 0.051 |
| Example VIII | 8.9 | 0.056 | 0.047 | 0.039 |
| Example IX | 4.0 | 0.120 | 0.095 | 0.041 |

This friction modifying ability of these sulfomolybdenum products was further demonstrated by their fuel efficiency results in vehicle tests. Utilizing steady state fuel efficiency tests sulfomolybdenum products which are typified by Examples I, Example VI and Example VIII were run at concentrations of 0.75 to 1.1 wt. % on top of commercial motor oil formulations. The vehicles utilized ranged from Ford Pintos with a 2.3l. engine to a Ford LTD II with a 350 cubic inch engine. At constant speeds of 30, 45 and 55 mph fuel efficiency increases of 0.6 to 7.1% in terms of miles per gallon were obtained.

The sulfomolybdenum products of the process of this invention are shown to have extreme pressure and anti-wear properties. These are shown in the following tables.

TABLE II

| Additive | Wt. % | Timken OK Load, lbs. | 4-Ball Weld, kg. | 4-Ball LWI, kg. |
|---|---|---|---|---|
| Blank | 1.0 | 20 | 160 | 32.3 |
| Example I | 1.0 | 35 | 200 | 42.0 |
| Example I | 5.0 | 55 | 400 | 57.0 |
| Example II | 5.0 | 45 | 250 | 46.4 |
| Example IV | 1.0 | 45 | 250 | 44.6 |
| Example IV | 5.0 | 60 | 620 | 105.6 |

TABLE III
(in Lithium Complex Grease)

| Additive | Wt. % | Timken OK Load, lbs. | 4-Ball Weld, kg. | 4-Ball LWI, kg. |
|---|---|---|---|---|
| Blank | — | 6 | 126 | 21.9 |
| Example VI | 2.0 | 50 | 250 | 46.2 |
| Example VIII | 2.0 | 50 | 250 | 53.2 |
| Example XII | 2.0 | 25 | 250 | 37.5 |

Having thus described our invention, we claim:

1. A process for the preparation of a lubricating oil or grease having wear resistant, extreme pressure and fuel efficient characteristics comprising the step of adding to a petroleum base or synthetic base oil or grease an effective amount of a sulfurized oxymolybdenum organophosphorodithioic compound which is the reaction product of the process which consists essentially of the steps of (A) reacting at reflux in an inert solvent for at least one hour in a temperature range of 160°–185° F. (1) an oxide of molybdenum which has been solubilized in the presence of a sulfurizing compound selected from the group consisting of sodium hydrosulfide and sodium monosulfide and (2) a dialkyldithiophosphoric acid, and then (B) recovering the reaction product.

2. The process of claim 1 wherein the reaction is continued for a period of time between 1 and 5 hours.

3. The process of claim 1 wherein the inert solvent consists essentially of at least one liquid selected from the group consisting of water, an alcohol and oil.

4. A process for the preparation of sulfurized oxymolybdenum organophosphorodithioic acid compounds which consists essentially of the steps of (A) reacting at reflux in an inert solvent for at least one hour in a temperature range of 160°–185° F. (1) an oxide of molybdenum which has been solubilized in the presence of a sulfurizing compound selected from the group consisting of sodium hydrosulfide and sodium monosulfide and (2) a dialkyldithiophosphoric acid, and then (B) recovering the reaction product.

* * * * *